(12) United States Patent
Yamaguchi et al.

(10) Patent No.: US 6,627,888 B2
(45) Date of Patent: Sep. 30, 2003

(54) SCANNING ELECTRON MICROSCOPE (75) Inventors: Satoru Yamaguchi, Hitachinaka (JP); Takashi Iizumi, Hitachinaka (JP); Osamu Komuro, Hitachinaka (JP); Hidetoshi Morokuma, Hitachinaka (JP); Tatsuya Maeda, Hitachinaka (JP); Juntaro Arima, Hitachinaka (JP); Yasuhiko Ozawa, Abiko (JP)

(73) Assignee: Hitachi, Ltd., Tokyo (JP)

( * ) Notice: Subject to any disclaimer, the term of this patent is extended or adjusted under 35 U.S.C. 154(b) by 262 days.

(21) Appl. No.: 09/792,721

(22) Filed: Feb. 23, 2001

(65) Prior Publication Data
US 2001/0019109 A1 Sep. 6, 2001

(30) Foreign Application Priority Data

Feb. 29, 2000 (JP) ........................................ 2000-058022

(51) Int. Cl.[7] ................................................ H01J 37/28
(52) U.S. Cl. ..................... 250/310; 250/307; 250/491.1
(58) Field of Search ................................ 250/307, 310, 250/491.1

(56) References Cited

U.S. PATENT DOCUMENTS 5,087,537 A * 2/1992 Conway et al. .......... 250/491.1

2002/0185598 A1 * 12/2002 Bowley et al. ............. 250/310

FOREIGN PATENT DOCUMENTS

| JP | 9-245709 | 9/1997 |
| JP | 2000-123771 | 4/2000 |
| JP | 2000-236007 | 8/2000 |

* cited by examiner

Primary Examiner—Jack Berman
(74) Attorney, Agent, or Firm—Kenyon & Kenyon (57) ABSTRACT An object of the present invention is to provide a scanning electron microscope for reducing a process concerning inspection positioning or an input operation, thereby functioning with high precision at high speed.

To accomplish the above object, the present invention provides a scanning electron microscope having a function for identifying a desired position on the basis of a pattern registered beforehand, which includes a means for setting information concerning the pattern kind, the interval between a plurality of parts constituting the pattern, and the size of parts constituting the pattern and a means for forming a pattern image composed of a plurality of parts on the basis of the information obtained by the concerned means.

9 Claims, 13 Drawing Sheets

| Design Value | |
|---|---|
| Kind | Hole |
| Diameter | 0.200 — (4101) |
| Pitch X | 0.200 — (4102) |
| Pitch Y | 0.200 — (4103) |
| Min Dameter | 0.200 — (4104) |
| Max.diameter | 0.200 — (4105) |
| OK | Cancle |

SCANNING ELECTRON MICROSCOPE

BACKGROUND OF THE INVENTION

1. Field of the Invention

The present invention relates to a scanning electron microscope and more particularly to a scanning electron microscope for suitably executing positioning to an inspection position on a semiconductor integrated circuit.

2. Discussion of the Background

In correspondence to recent integration of semiconductor devices, a scanning electron microscope is used for observation and inspection of a refined circuit pattern. A scanning electron microscope (hereinafter referred to as CD-SEM) for measuring the size of a specific pattern used on the semiconductor manufacture line is promoted in automation so as to prevent raising of dust by a person in the same way as with other devices or to improve the processing capacity.

In order to automatically measure a target pattern on a wafer, a procedure of moving the observation view field to an approximate position by stage movement, precisely obtaining the measuring pattern position from the observation view field, moving the view field to the position, and measuring the pattern is used. To execute automatic operation, the aforementioned sequence is stored as a file (hereinafter referred to as a recipe file) and at the time of automatic operation, the recipe file is read and the sequence is executed automatically. To detect the precise position of the measuring pattern, the image part (hereinafter referred to as a template) including a characteristic pattern as a guide is registered beforehand and the position is decided by the distance from the pattern position detected by template matching.

In Japanese Patent Application Laid-Open 9-245709, an art for registering a template as a guide beforehand and deciding the target measuring pattern position by matching using the template is disclosed.

SUMMARY AND OBJECTS OF THE INVENTION

A problem as indicated below is imposed in inspection positioning of a sample by the template matching method.

Firstly, to execute template matching, as mentioned above, it is necessary to register a template as a guide beforehand. However, to register a template for template matching, it is necessary to set an environment for introducing and observing a sample such as a semiconductor wafer into a sample chamber. Further, to search for a pattern as a template, a considerable time is required.

In actual positioning by template matching, a normalization correlation value is obtained for the front of an image including a registered pattern and an image to be detected, so that the portion having no information in the template and the noise portion are also calculated. As a result, an incorrect position may be detected due to noise, charge-up of a sample, or uneven contrast.

An object of the present invention is to provide a scanning electron microscope for reducing a process concerning inspection positioning or an input operation, thereby functioning with high precision at high speed.

The present invention, to accomplish the above object, provides a scanning electron microscope having a function for detecting a pattern on the basis of electrons obtained by scanning an electron beam on a sample and identifying a desired position on the basis of the detected pattern and a pattern registered beforehand, which is characterized in that the microscope has a means for setting information concerning the pattern kind, the interval between a plurality of parts constituting the pattern, and the size of parts constituting the pattern and a means for forming a pattern image composed of a plurality of parts on the basis of the information obtained by the concerned means.

By use of such a constitution, a template can be registered without setting an observation environment of a scanning electron microscope such as evacuation. Particularly, with respect to a pattern having a properly regulated arrangement like a line pattern or a hole pattern formed on a semiconductor wafer, if there is information for identifying the size of a plurality of parts forming the pattern and the relative position relationship available, the pattern image can be identified.

The present invention takes up this point, has a constitution of selectively inputting a necessary condition, and forms a pseudo-pattern on the basis of it, so that conventional image forming using an actual pattern image is unnecessary and the operation time can be contracted greatly.

Furthermore, the present invention, to accomplish the above object, provides a scanning electron microscope having a function for detecting a pattern on the basis of electrons obtained by scanning an electron beam on a sample and identifying a desired position on the basis of the detected pattern and a pattern registered beforehand, which is characterized in that the microscope has a means for recognizing the number of detected patterns and/or the interval between a plurality of parts of the detected patterns, a means for calculating the evaluation value on the basis of comparison of the number recognized by the concerned means with the number of registered patterns, and/or a means for calculating, on the basis of comparison of the interval recognized by the means with the interval between the parts of the registered patterns, the evaluation value based on the consistency.

For example, when a pattern composed of a plurality of parts (line patterns or hole patterns) is crushed and the line patterns or the hole patterns are in contact with each other, the pattern is one that length measurement and inspection of the line or hole patterns are not necessary and pattern matching is difficult. According to the present invention, when the number of line patterns and/or the interval are structured so as to evaluate selectively, it can be judged whether each pattern is suitable for length measurement and inspection.

DETAILED DESCRIPTION OF THE PREFERRED EMBODIMENTS

With respect to an image obtained by the scanning electron microscope, many secondary signals are emitted from the pattern edge (edge effect), so that the information of the edge is main. The pattern edge in an image is extremely smaller in an area than the whole image, though it includes most pattern information of a sample. Inversely, the part other than the edge has no pattern or includes much noise having little information used for positioning.

A general template matching method identifies a pattern using the template. However, the template matching method obtains a normalization correlation value for a registered image portion and all images to be detected, so that the part (part having no edge) having no information in the template and the noise portion which is not information are also calculated. As a result, an incorrect position may be detected due to noise, charge up, or uneven contrast.

Particularly, on the semiconductor manufacture line, in order to obtain most suitable manufacture conditions (for example, stepper exposure time, variations of the focus, etc.), a test wafer having conditions changed for each chip (hereinafter referred to as a conditional wafer) is prepared.

CD-SEM is used for inspection of this conditional wafer. The pattern of the conditional wafer to be observed for each chip becomes a pattern greatly different in the pattern form as the manufacture conditions are shifted more from the most suitable manufacture conditions. Depending on the conditions, a resist remains, and adjacent patterns are connected to each other, and any pattern gets thin and comes down, and the number of patterns decreases. When the pattern form and count are changed like this, it is difficult to detect them using the template matching method.

When the template is to be registered, it is necessary to actually observe the sample pattern, form an image, and preserve the image portion. For a conditional wafer, an operation of registering a plurality of templates is generated. To select a pattern as a guide or decide a most suitable magnification factor, skill is required. Furthermore, decision of success or failure of detection is made only by a normalization correlation value.

Therefore, when the normalization correlation value is more than the threshold value even if the number of patterns is changed, the position having no existing pattern is measured.

The equipment of this embodiment of the present invention performs a process relating to template matching using information concerning the numerical value of the pattern form and information concerning the position relationship, thereby can solve the aforementioned problem.

The embodiment of the present invention will be explained hereunder with reference to the accompanying drawings.

Figure 1:
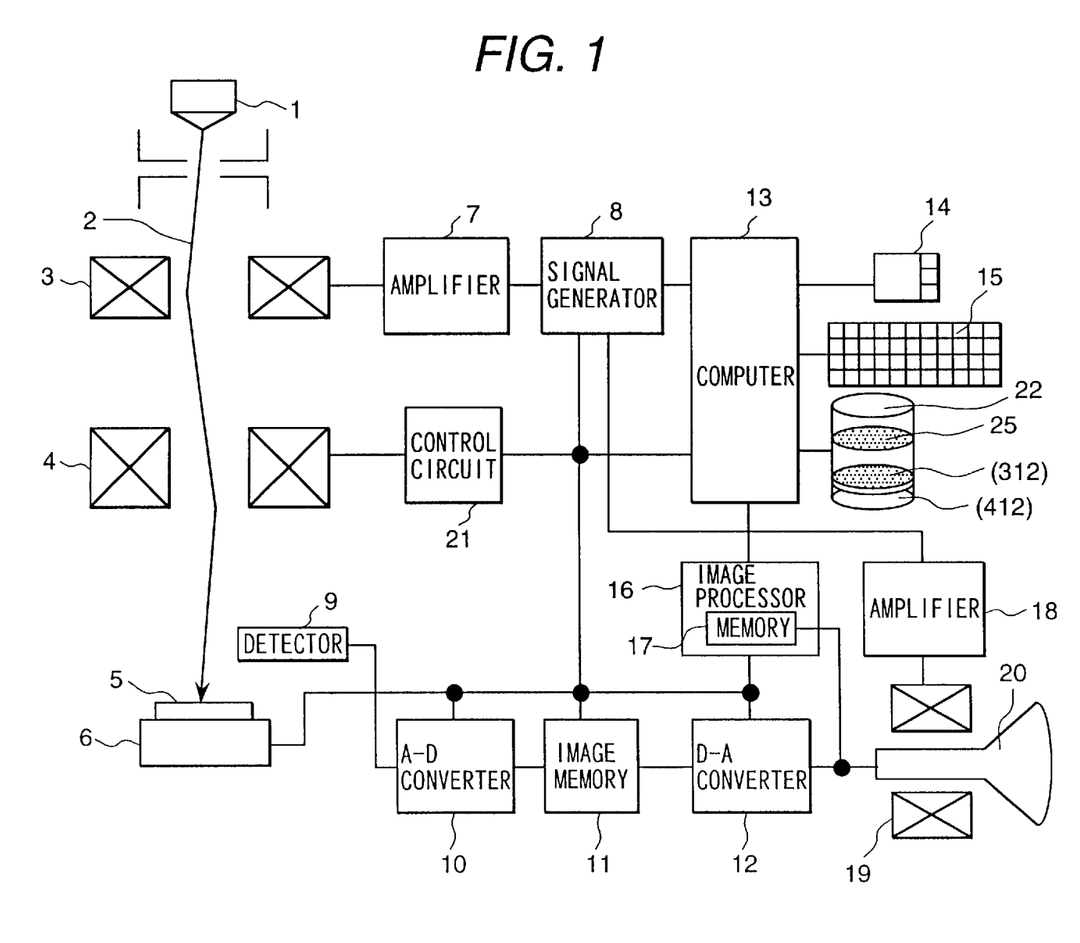
FIG. 1 is a schematic view of an embodiment of the present invention.

FIG. 1 is a schematic view of the scanning electron microscope of the present invention. An electron beam 2 emitted from an electron gun 1 is deflected by a deflecting coil 3, then limited thinly by an object lens 4, and irradiated onto a sample wafer 5 on a stage 6. The object lens 4 is controlled by an object lens control circuit 21 which can be controlled from a host computer 13.

The scanning range and scanning position on the sample wafer 5 can be changed by a deflecting signal which is generated by a deflecting signal generator 8, amplified by a deflecting amplifier 7, and supplied to the deflecting coil 3.

Secondary electrons emitted from the sample wafer 5 by incoming of the electron beam 2 is converted to an analog electric signal by a detector 9, converted to a digital signal by an A-D converter 10, and then stored in an image memory 11. The contents of the image memory 11 are always converted from a digital signal to an analog signal by a D-A converter 12 and applied to the grid as a luminance signal of a CRT 20. At this time, the A-D converter 10, the image memory 11, and the D-A converter 12 receive a timing signal for converting an image signal from analog to digital, further converting from digital to analog, and displaying it as an image from the deflecting signal generator 8.

A deflecting coil 19 of the CRT 20 is excited by a deflecting amplifier 18 according to a deflecting signal of the deflecting signal generator 8. The magnification factor is decided by the display width and scanning range of the CRT 20. An image processor 16 is controlled by a signal from the host computer 13. The contents of the image memory 11 are transferred and processed by an image memory 17 of the image processor 16.

Figure 2:
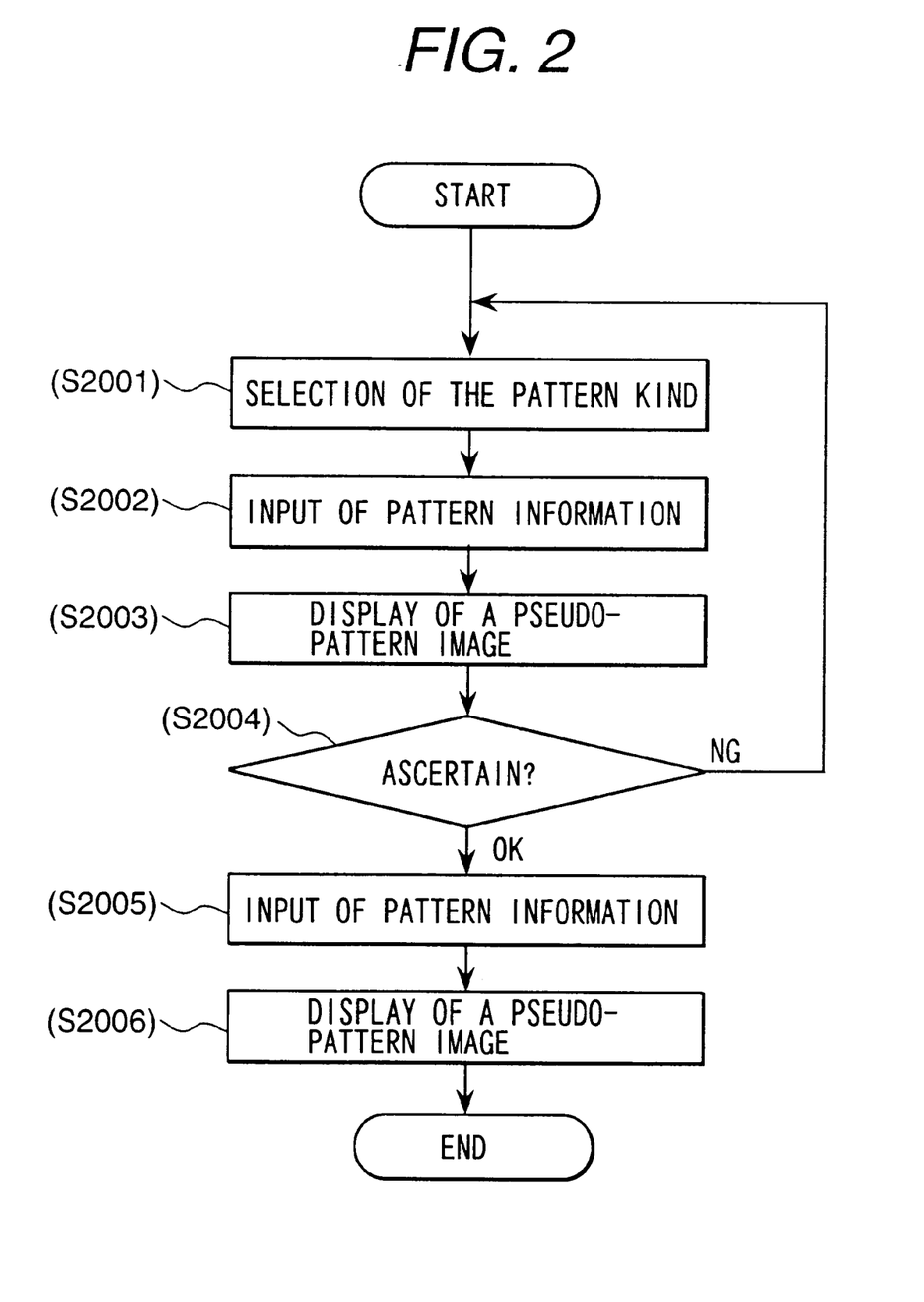
FIG. 2 is a drawing for explaining the registration sequence.
Figure 3A:
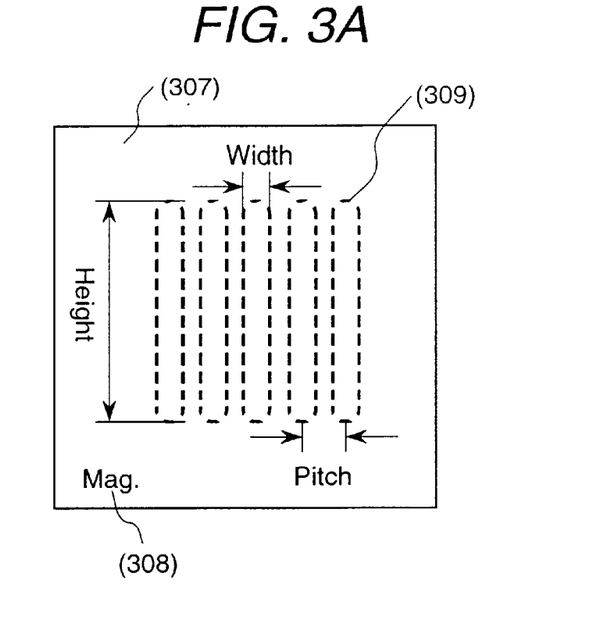
FIGS. 3A and 3B are drawings for explaining an example of a registration screen for registering form information and position information.
Figure 3B:
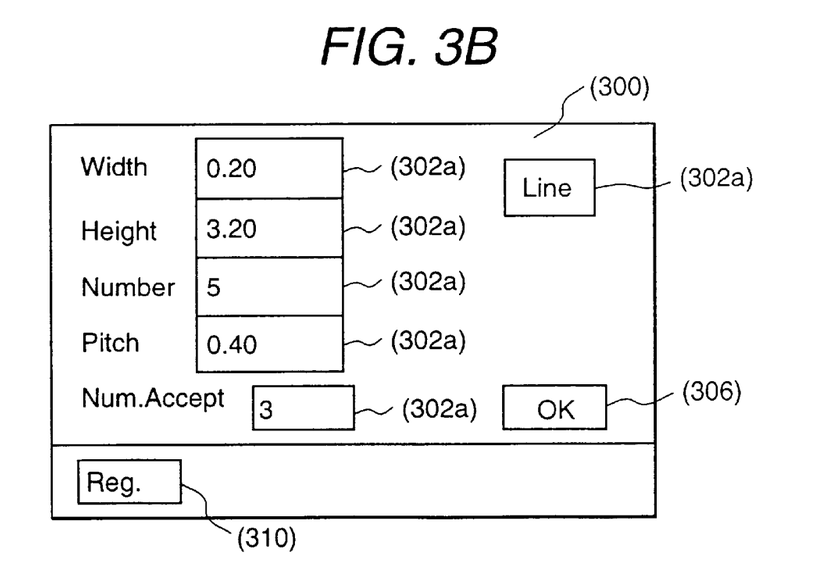

The sequence of the present invention for registering pattern form information (pattern kind, pattern height, width, etc.) and position relationship (interval between patterns, etc.) is shown in FIG. 2. FIGS. 3A and 3B are drawings showing registration screen examples for registering the form information and position relationship according to the sequence shown in FIG. 2.

The host computer 13 displays a registration screen on the CRT 20 according to a signal from a mouse 14 or a keyboard 15. There is a menu (301) for selecting the pattern kind on the screen and the line patterns and hole patterns can be selected (S2001).

A user inputs pattern information to an input window (302a) of the line width Width (302), an input window (303a) of the line length Height (303), an input window (304a) of the line number Number (304), and an input window (305a) of the pitch Pitch (305) between line patterns respectively from the keyboard 15 (S2002) and then presses an OK button (306). The host computer 13 obtains a magnification factor Mag (308) from Formula (1) on the basis of the values of (302) to (305). Furthermore, the host computer 13 prepares a pseudo-pattern (309) to be displayed on the image when it is observed at the obtained magnification factor and displays it on the CRT 20 as an image (307) together with Mag (308) (S2003). A display example is shown in FIG. 3($a$). The user ascertains the input value by the pseudo-pattern (309) (S2004). When there is a contradiction, the user repeats the steps (S2001 to S2004). When there is no contradiction, the user inputs the threshold value of number (311) Num.Accept. at the time of detection to an input window (311a) (S2005) and presses a registration button (310). Upon receipt of this signal, the host computer 13 preserves the input information (302) to (305), the magnification factor (308), and the threshold value of number (311) Num.Accept. in a storage unit 22 as a line detection file (312) in association with a recipe file 25 (S2006).

$$1wp=\min(\text{Width}, \text{Pitch}-\text{Width})(nm)$$

$$\text{Mag.}=1p\min \times rw/(pw \times 1wp) \quad \text{Formula (1)}$$

where

1wp: a smaller value between 1w and 1p−1w, rw: width of the image display area, pw: width of a display image (pixel), and 1pmin: minimum processing width (pixel).

Figure 4A:
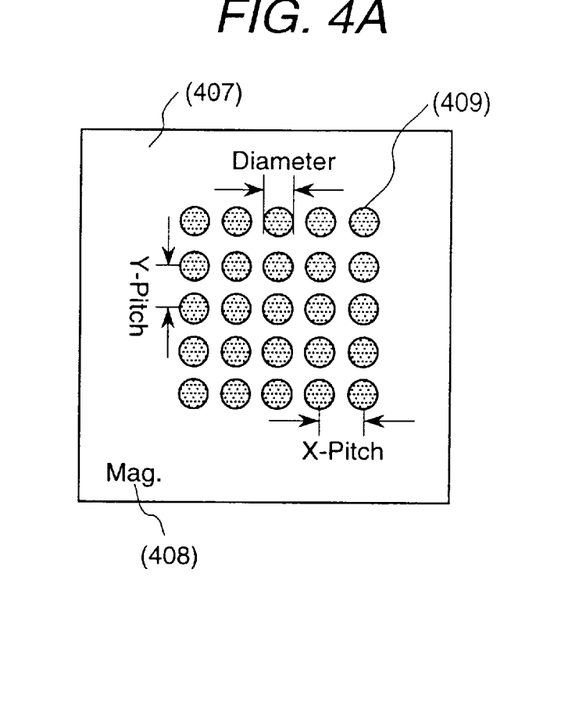
FIGS. 4A and 4B are drawings for explaining an example of a registration screen for registering form information and position information.
Figure 4B:
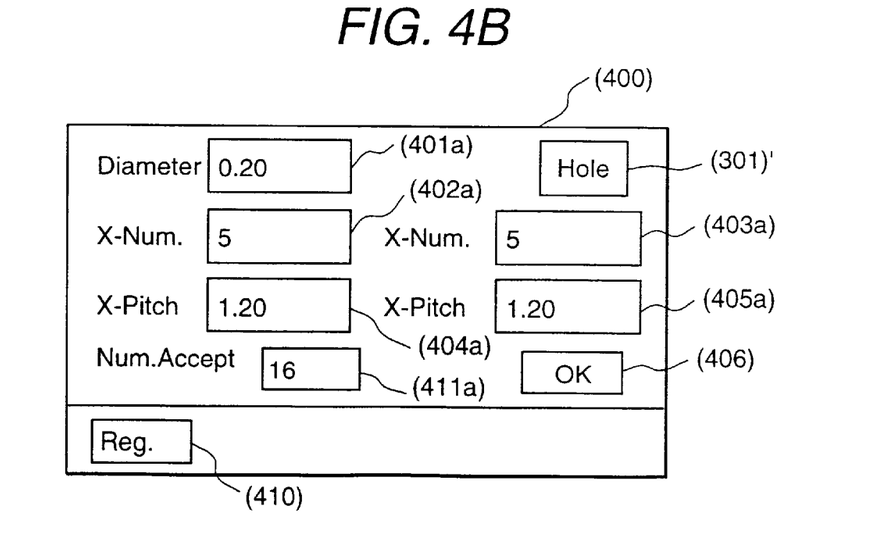

A screen example (400) when holes are selected is shown in FIGS. 4A and 4B. The user inputs pattern information to an input window (401) of the hole diameter Diameter, an input window (402) of the number in the direction x (column) X-Num., an input window (403) of the number in the direction y (row) Y-Num., an input window (404) of the pitch in the direction x (column) X-Pitch, and an input window (405) of the pitch in the direction y (row) Y-Pitch respectively from the keyboard 15 (S2002) and then presses an OK button (406). The host computer 13 prepares a pseudo-pattern (409) on the basis of the values of (401) to (405). Furthermore, the host computer 13 obtains a magnification factor Mag. (408) by Formula (2) and displays it on the CRT 20 together with the pseudo-image (409) (S2003).

A display example is shown in FIG. 4A. The user ascertains the input value by the pseudo-image (407) (S2004). When there is a contradiction, the user repeats the steps (S2001 to S2004). When there is no contradiction, the user inputs the threshold value of number Num.Accept. at the time of detection to an input window (411) (S2005) and presses a registration button (410). Upon receipt of this signal, the host computer 13 preserves the input information (401) to (404) and the magnification factor (408) in the storage unit 22 as a line detection file (412) in association with the recipe file 25 (S2006).

$$harea=\max((hnx-1) \times hpx, (hny-1) \times hpy)(nm)$$

$$mag=rw/(harea \times 2) \quad \text{Formula (2)}$$

where harea: a larger value between (hnx−1)×hpx and (hny−1)×hpy and rw: width of the image display area.

Figure 12:
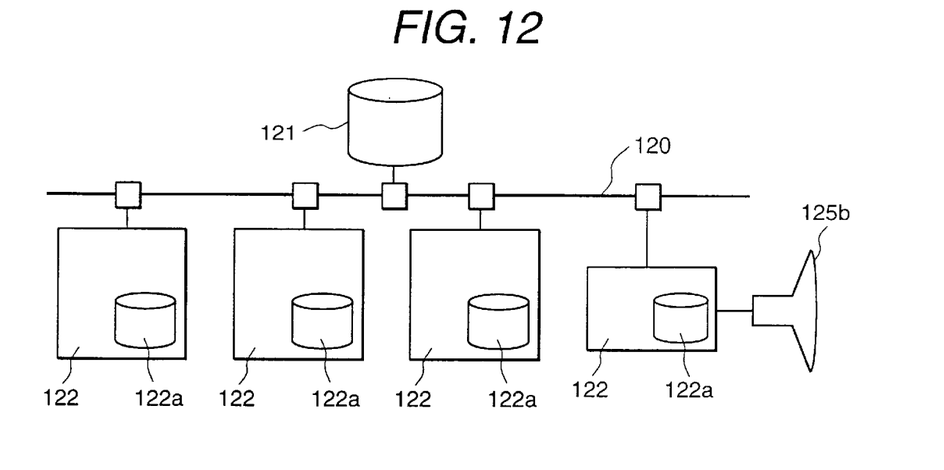
FIG. 12 is a drawing showing an example that the scanning electron microscope of this embodiment is connected to a network.

The pattern form information and position relationship can be read via a network 120 connected to the host computer 13. The pattern form information and position relationship can be read from a storage unit 121 of a file server and a storage unit 123a or 124a of a manufacture condition file of a manufacturing device 123 or a manufacture condition file of another manufacturing device 124.

Figure 5:
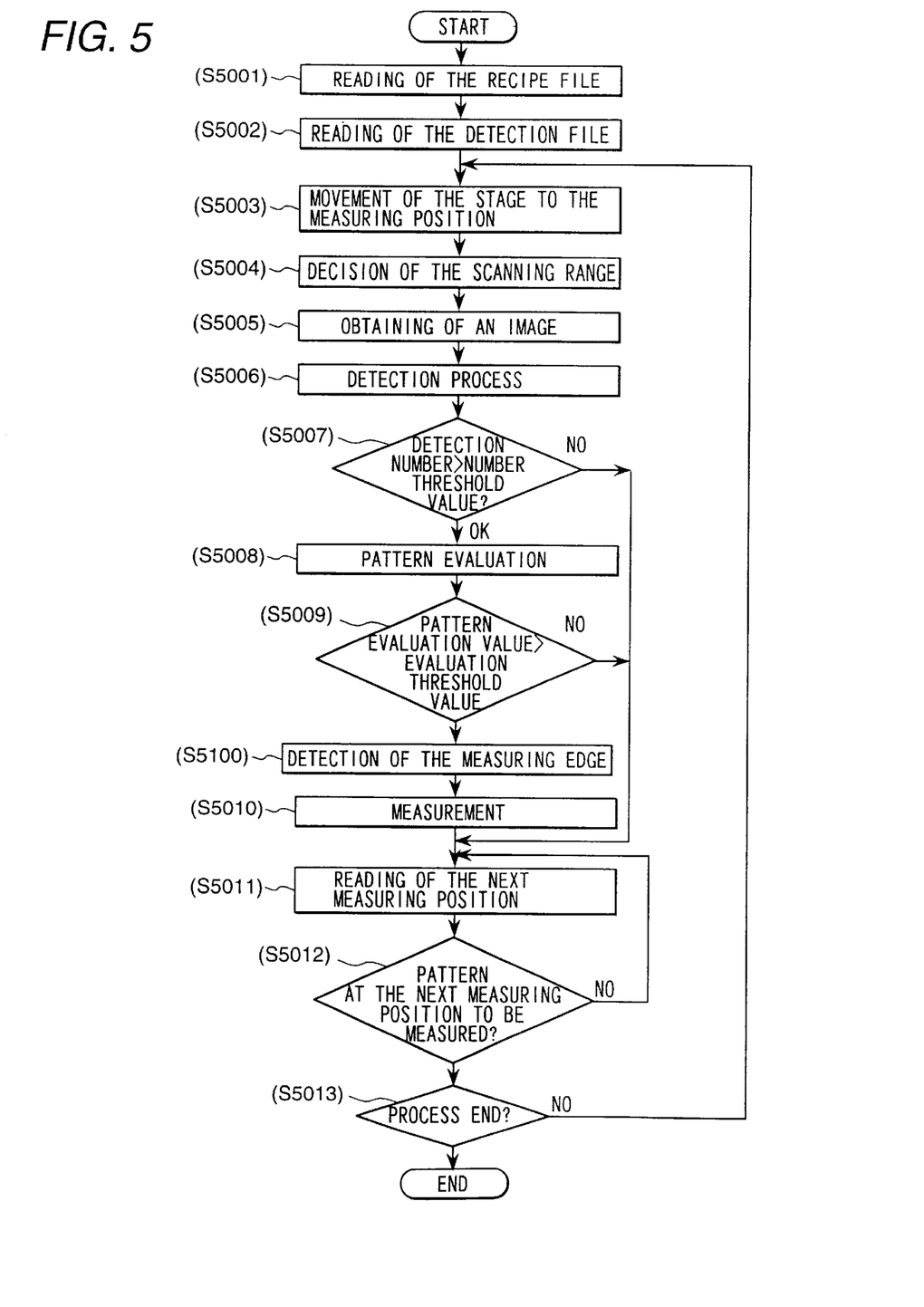
FIG. 5 is a drawing for explaining the steps for detecting a pattern.

The sequence of the present invention for detecting patterns using the pattern form information and position relationship is shown in FIG. 5. The host computer 13 reads the recipe file 25 designated by the mouse 14 or the keyboard 15 by a user from the storage unit 22 (S5001) and reads the line detection file (312) (or the hole detection file (412)) in association with the recipe file 25 at the same time (S5002).

The host computer 13 sends a drive signal to the stage 6 from the measuring position information registered in the recipe file 25 beforehand and moves the stage 6 to the measuring position (S5003). In this case, the pattern form information and position relationship are transferred to the image processor 16. The host computer 13 decides the scanning range on the sample wafer 5 according to the magnification factor (308) (S5004). The host computer 13 irradiates an electron beam onto the sample wafer 5 by a deflecting signal which is generated by the deflecting signal generator 8, amplified by the deflecting amplifier 7, and supplied to the deflecting coil 3 on the basis of the scanning range and obtains an image in the image memory 17 according to the aforementioned procedure (S5005).

Upon receipt of a detection processing signal from the host computer 13, the image processor 16 executes the detection process (S5006) and returns the number of detected patterns to the host computer 13. The host computer 13 compares it with the threshold value of number (313) (S5007) and when the number of detected patterns is larger than the threshold value of number (313), the image processor 16 executes pattern evaluation. The reason for that the pattern evaluation is executed when the number of detected patterns is larger than the threshold value of number is that mixing of noise is taken into account. However, the image processor 16 may be structured so as to execute evaluation only when both numbers are the same.

When the number of detected patterns is smaller than the threshold value of number (313), the host computer 13 skips pattern evaluation and measurement. The image processor 16 executes pattern evaluation according to this instruction and returns the evaluation value to the host computer 13. The host computer 13 compares it with the threshold value of pattern evaluation of the recipe file 25 and decides whether the patterns can be measured (S5009). One condition of the evaluation threshold value is the threshold value of number (313) explained previously.

When the patterns can be measured, the host computer 13 detects the measuring edge (S5100) and then measures the patterns (S5010) and when it judges as unmeasurable, it skips measurement. By use of such a constitution, unnecessary calculation and scan can be prevented and even if the number of patterns is reduced in a stepper conditional wafer, the patterns are detected and neighboring patterns which are connected to each and must not be measured can be prevented from measurement, so that useless processes can be reduced and the processing speed can be increased.

When the patterns are detected using the-numerical information of pattern form and the position relationship, patterns that the form is greatly changed and the number of patterns is also changed like conditional patterns can be detected. Furthermore, since the numerical information of pattern form and the position relationship are used, a template using an actual pattern image is not registered, so that the OFF line can be registered. Further, there is no need to select a pattern as a guide requiring experience and numerical data is directly input, so that the registration operation can be simplified. Since the operation is performed according to the threshold value input beforehand on the basis of the pattern evaluation value, the sequence can be optimized.

When the aforementioned series of processes is finished, the host computer 13 reads the next measuring position from the recipe file 15 (S5011). The host computer 13 executes measurement from the most suitable measuring position on the basis of the information of the manufacture condition files from the manufacture devices 123 and 124. The next measuring position is decided on the basis of the number of detected patterns and pattern evaluation value. For example, the host computer 13 judges the direction of the pattern form getting worse from the number of detected patterns and pattern evaluation value and does not move to the measuring position outside the measuring position where the number of detected patterns is smaller than the threshold value (S5012). By doing this, useless processes can be prevented from execution and the processing speed is increased.

Figure 8A:
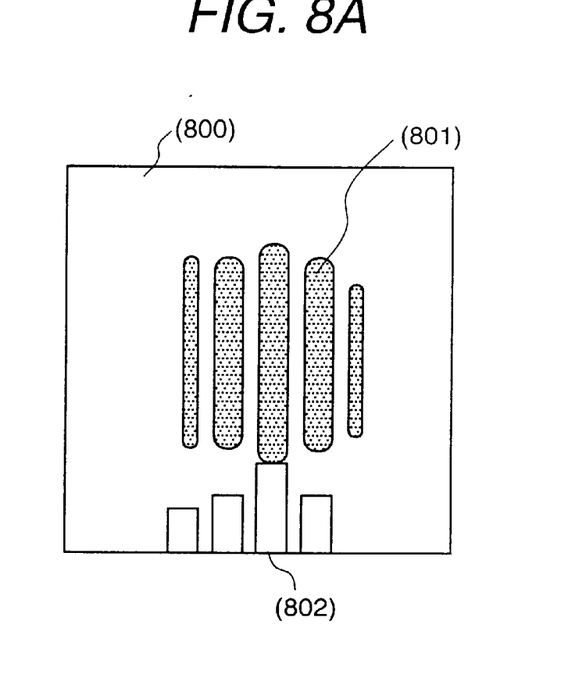
FIGS. 8A and 8B are drawings showing a display example of evaluation results of form information and position information.
Figure 8B:
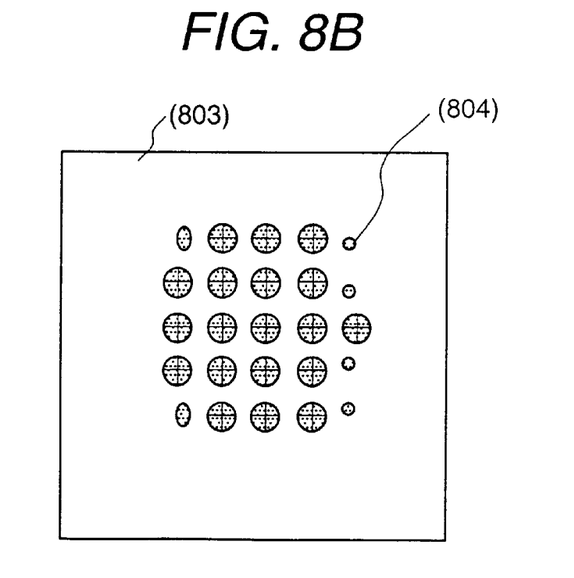

The image processor 16 displays results on the image memory 17 using the detected pattern position, pattern form information, position relationship, and mapping images. A display example of results is shown in FIG. 8. In the case of the line pattern, results are displayed as the line pattern image (800) shown in FIG. 8A. When the detected pattern is like (801), the evaluation value a of the mapping images corresponding to the respective line pattern positions obtained from the detected pattern position is displayed like a graph (802). The height of each of the bar graphs indicates a ratio on the basis of the maximum value of the evaluation value a of the mapping images. In the case of the hole pattern image (803), a cross mark (804) is displayed as shown in FIG. 8(b). The difference in the evaluation value of each pattern is reflected in the size of the cross mark.

Figure 6:
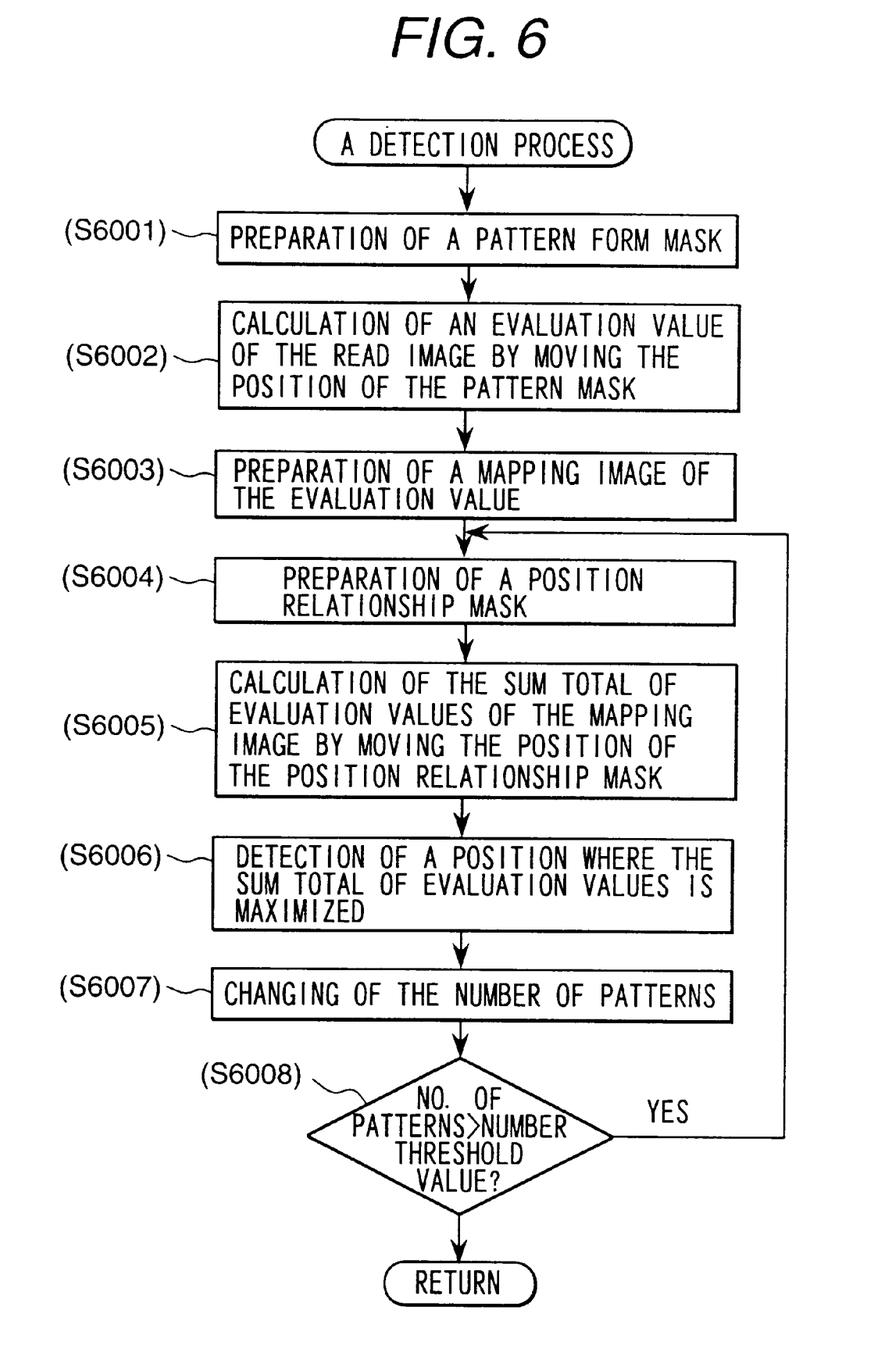
FIG. 6 is a drawing for explaining the detection processing steps of an image processing unit.

The detection process of the image processor 16 using the pattern form information and position relationship is shown in FIG. 6. The image processor 16 prepares a pattern mask of the pattern form to be detected from the pattern width (301) and pattern height (302) of the pattern form information (S6001). The pattern mask is one pattern part shown in FIGS. 4(a) and 4(b). The image processor 16 calculates the evaluation value a by shifting the pattern mask in position overall the image of the image memory 17 (S6002) and prepares a mapping image that the calculated evaluation a is arranged in correspondence with the pattern mask position (S6003). The evaluation value a is calculated by Formula (3) or Formula (4) and Formula (5).

$$r(X, Y) = \frac{\left[N \sum_{i,j} P_{ij} M_{ij} - \left(\sum_{i,j} P_{ij}\right)\left(\sum_{i,j} M_{ij}\right)\right]}{\sqrt{\left[N \sum_{i,j} P_{ij}^2 - \left(\sum_{i,j} P_{ij}\right)^2\right]\left[N \sum_{i,j} M_{ij}^2 - \left(\sum_{i,j} M_{ij}\right)^2\right]}}$$ Formula (3)

where $P_{ij}$ indicates a density value at the point (X+i, Y+i) corresponding to the pattern mask of the line pattern image (800) or the hole pattern image (803), and $M_{ij}$ indicates a density value at the point (X+i+1, Y+j+1), and N indicates the number of pixels of the pattern mask.

$$\frac{\sum_i \sum_j |P_{i,j} - P_{i+1,j}| + |P_{i,j} - P_{i+j+1}|}{N}$$ Formula (4)

where $P_{ij}$ indicates a gradation value of the line pattern image (800) or the hole pattern image (803) and N indicates a total number of pixels of the pattern mask.

$$\frac{\sum (P_{ij} - P_{avg})^2}{N-1}$$ Formula (5)

where $P_{ij}$ and $P_{avg}$ indicates mean values in the pattern mask corresponding to the gradation value of the line pattern image (800) or the hole pattern image (803) and N indicates a total number of pixels of the pattern mask.

Figure 9A:
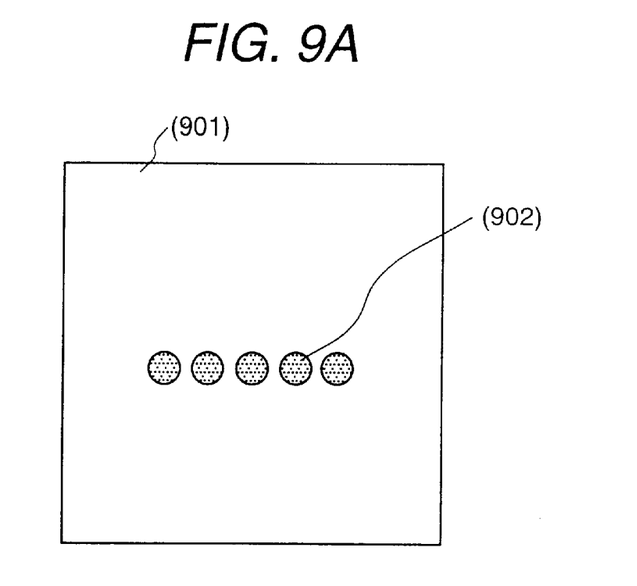
FIGS. 9A and 9B are drawings showing examples of a position relationship image and a position relationship mask of a hole pattern.
Figure 9B:
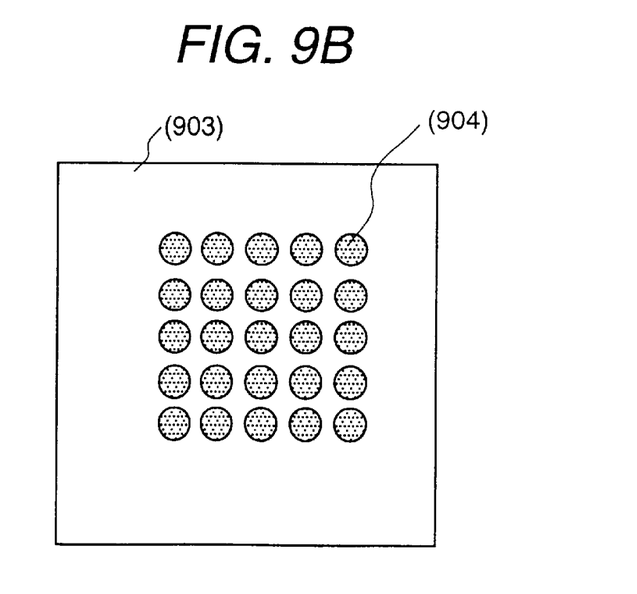

Next, the image processor 16 prepares a position relationship mask from a plurality of patterns (303) and position relationship (Pitch (304)) (S6004). The line pattern position relationship image (901), the line pattern position relationship mask (902), the hole pattern position relationship image (90), and the hole pattern position relationship mask (90) corresponding to FIGS. 4A and 4B are shown in FIGS. 9A and 9B. The image processor 16 obtains the sum total of evaluation values a by shifting the position of the prepared position relationship mask on the mapping image (S6005). The position where the sum total of evaluation values a is maximized is the position to be detected (S6006). With respect to the position relationship mask, in consideration of reduction of the number of patterns, the image processor changes the number of patterns by the number of patterns (303)~the threshold value (311) and repeats S6004 to S6006. By the aforementioned process, the number of patterns and the detection position can be obtained.

Figure 7:
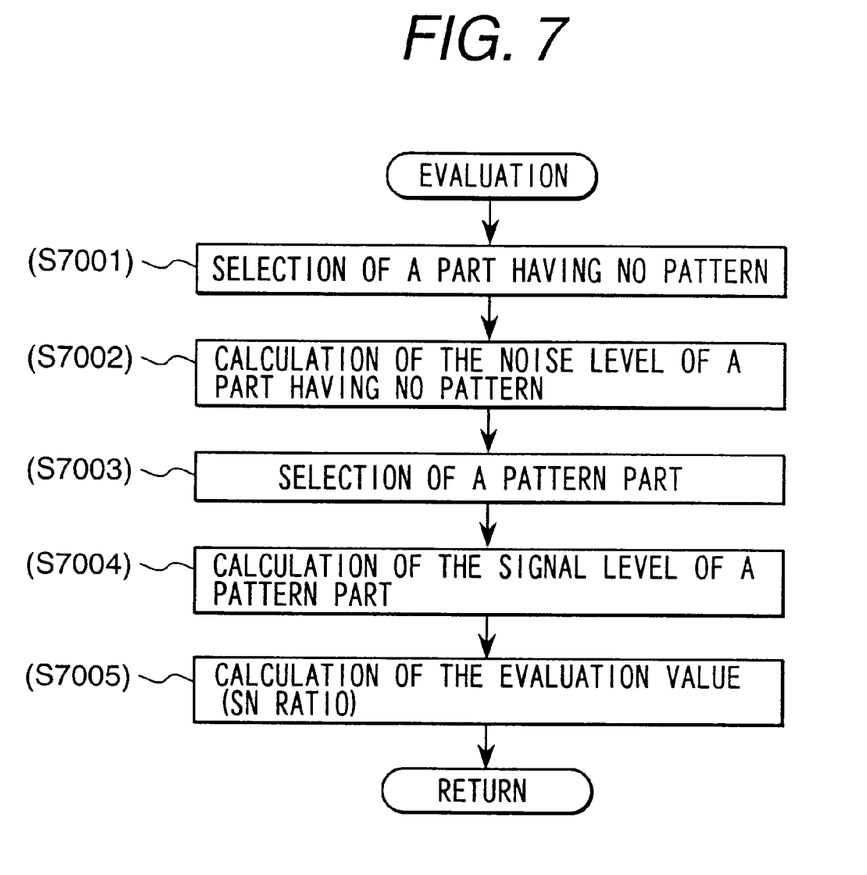
FIG. 7 is a drawing for explaining the pattern form evaluation procedure.

The evaluation procedure for the pattern form by the image processor 16 is shown in FIG. 7. The image processor 16 selects the part having no pattern from the prepared mapping image prepared at S6003 (S7001). With respect to selection of the part having no pattern, for example, the half value of the maximum value of the mapping image is set as a threshold value and the part below the threshold value is selected. The noise level (for example, dispersion) of the part having no pattern is calculated by Formula (5) (S7002).

Next, the image processor 16 detects the part where the pattern form is easily changed from the position detected at S6006 and calculates the signal level (for example, dispersion) obtained at S7003 (S7004). This part may be often set between patterns. The image processor 16 obtains the evaluation value b (SN ratio) from the noise level and signal level obtained at S7002 and S7003 and returns it to the host computer 13. Also for the hole patterns, the pattern position, number of patterns, and evaluation value b can be obtained according to the same procedure.

Figure 10A:
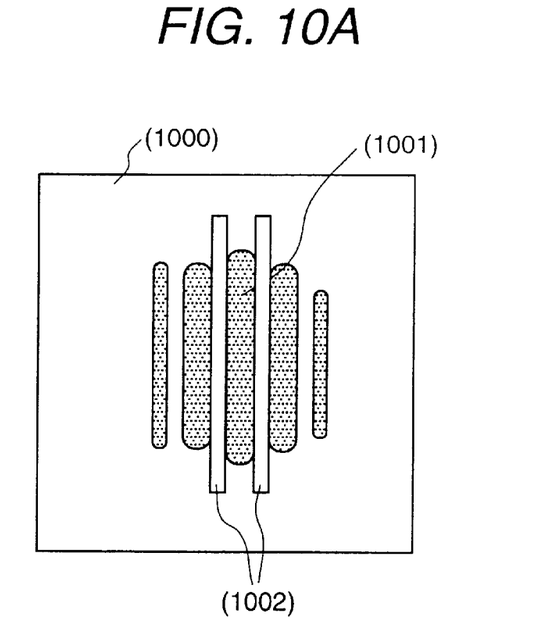
FIGS. 10A and 10B are drawings showing scan range examples of a hole pattern.
Figure 10B:
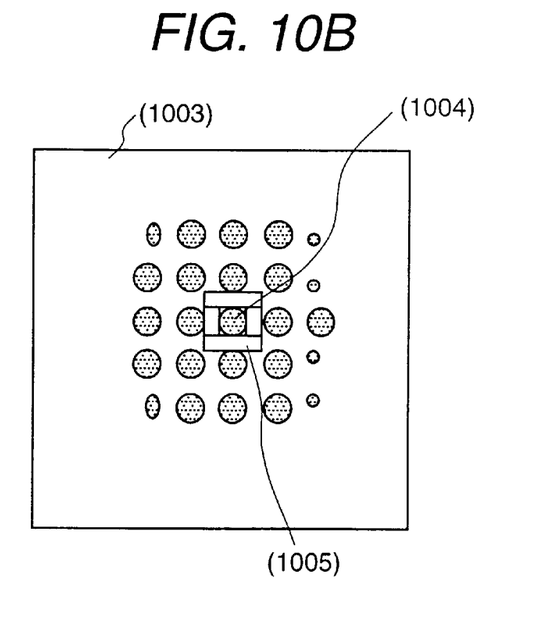

An embodiment that the electron beam scanning range is changed from input information in accordance with the pattern form will be explained hereunder. This process is used to receive a signal from a part where the pattern form is easily changed (S7004) or to detect a measuring edge (S5100). To receive a signal from a part where the pattern form is easily changed, the host computer 13 decides the scanning range using the position, line width (302), and pitch (305) which are detected as S6006 (in the case of the hole pattern, the hole diameter (401) and pitches in the directions x and y (404) and (405)). The scanning range examples of the line pattern and hole pattern are shown in FIG. 10.

Figure 11A:
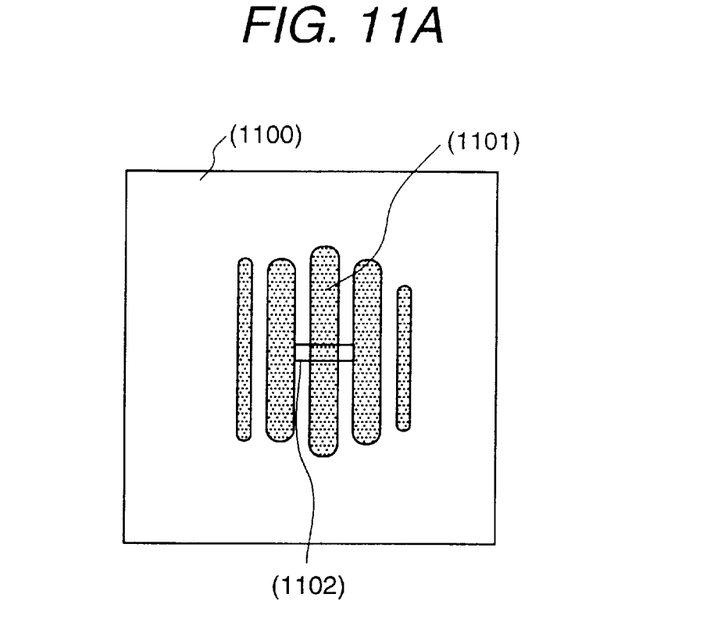
FIGS. 11A and 11B are drawings showing scan range examples when a measuring edge is to be detected.
Figure 11B:
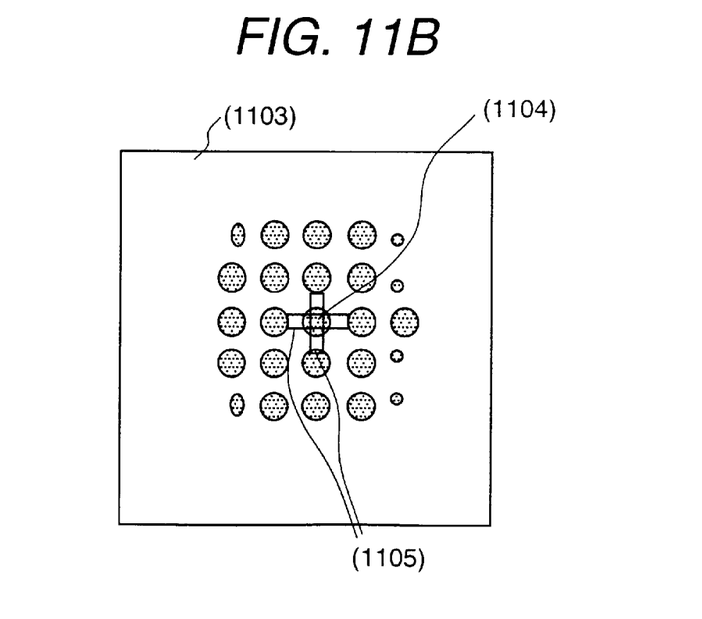

Assuming that the measuring pattern is (1001) in the line pattern image (1000), the evaluation scanning range is the position of (1002). Assuming that the measuring pattern is (1004) in the hole pattern image (1003), the evaluation scanning range is (1005). When the scanning range example of detection of a measuring edge is shown in FIG. 11. Assuming that the measuring pattern is (1101) in the line pattern image (1100), the edge detection scanning range is the position of (1102). Assuming that the measuring pattern is (1104) in the hole pattern image (1103), the edge detection scanning range is (1105).

By the device of this embodiment of the present invention, the observation magnification factor can be automatically decided by changing the area for scanning a sample to be detected from numerical value information of another pattern form whose observation magnification factor is to be changed and the most suitable scanning direction can be automatically decided to obtain an evaluation value from the pattern form.

Further, since an unnecessary electron beam is not scanned, contamination caused by an electron beam can be reduced. Since the numerical information of the pattern form and position relationship are detected in consideration of the edge, they are hardly affected by the charge-up and uneven contrast which are unique to the electron microscope. Since the pattern form and position relationship are input as numerical values in the registration operation, the detection of a pattern as a guide requiring experience and setting of magnification factor are not required. Since it is not necessary to actually observe a pattern on a wafer and register a template, a recipe file can be prepared offline.

Figure 13:
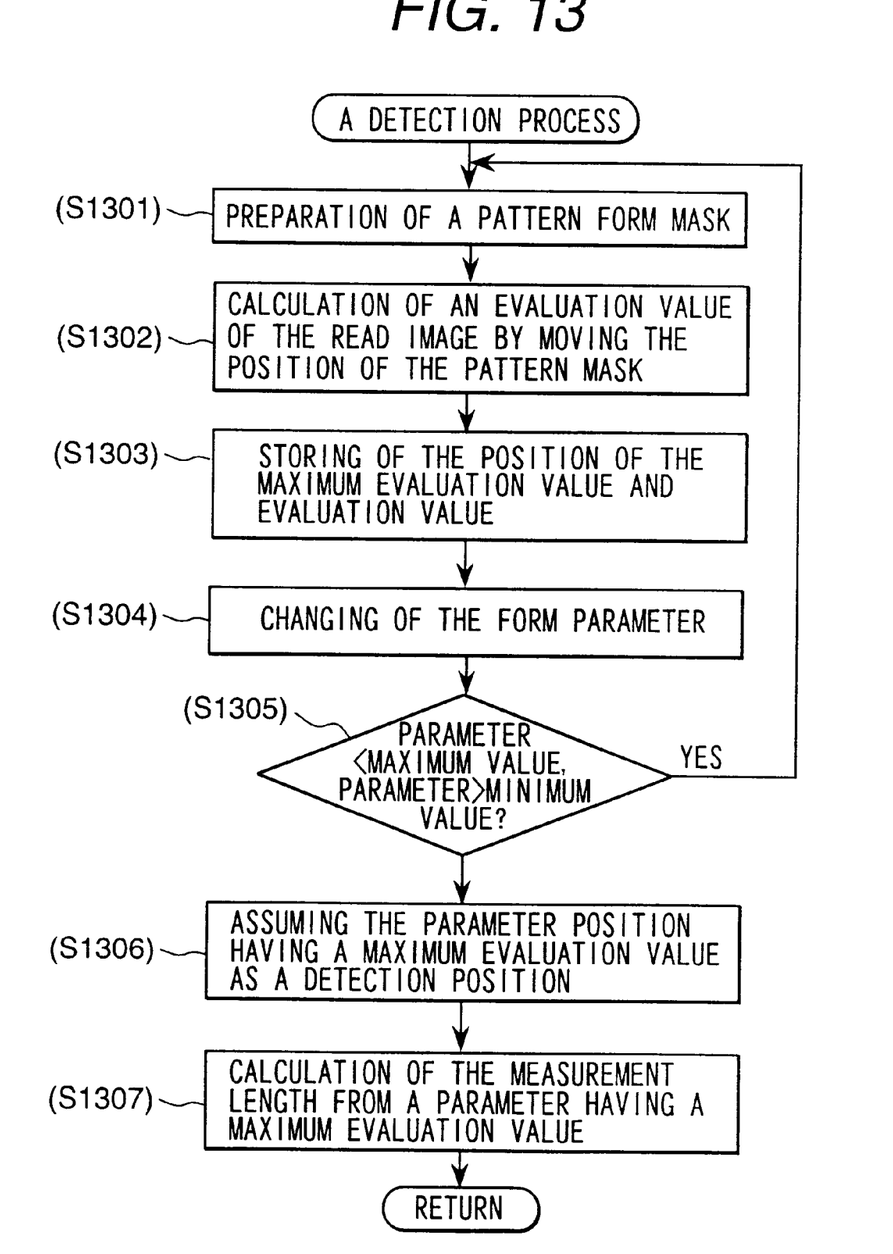
FIG. 13 is a drawing showing the detection procedure of a hole pattern.

The detection method of hole patterns at the magnification factor for measuring the length will be explained by referring to FIGS. 13 and 14. The detection method inputs the parameter range corresponding to changes in the pattern form, thereby can obtain also the roundness and area of holes. Here, the size change of the hole diameter will be explained. The detection method prepares a pattern mask from the hole diameter (S1301). The method scans the mask pattern for an image (4106) read into the image memory 17 of the image processor 16, thereby calculates an evaluation value using Formula (S1302). The method stores the position where the evaluation value is maximized and the evaluation value (S1303) and changes the form parameter (hole diameter in this case) (S1304). When the parameter is within the designated range, the method repeats S1301 to S1305. The parameter position having the maximum evaluation value among the parameters obtained according the aforementioned procedure is the detection position (S1306). Furthermore, the measurement length can be calculated from the parameter having the maximum evaluation value (S1307).

Figure 14A:
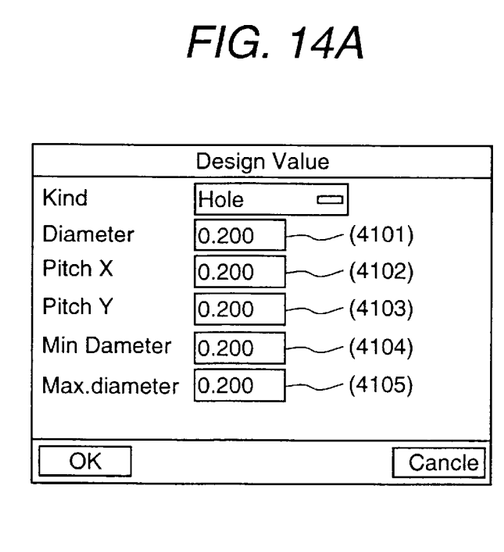
FIGS. 14A and 14B are drawings showing an example of a registration screen for registering hole pattern information.
Figure 14B:
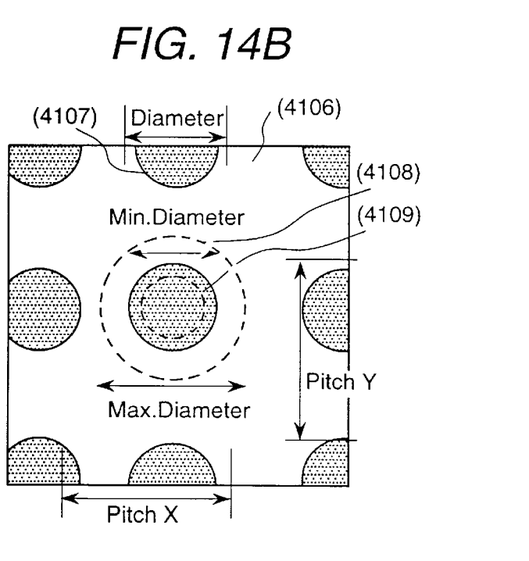

Boundary lines 4108 and 4109 for specifying the parameter range may be set by numerical value input on the numerical value input screen shown in FIG. 14A or may be set on the pattern model display shown in FIG. 14B. In this case, the boundary lines 4108 and 4109 displayed on the display device are set by changing and moving by a pointing device not shown in the drawing.

The device of this embodiment has a function for displaying an actual SEM screen on the display device in accordance with the setting screen shown in FIGS. 14A and 14B. By this display, for example, when a pattern different from the design data is formed due to an error in a semiconductor manufacture device, parameter setting according to an actual objective pattern can be executed. Furthermore, when a pattern model is also displayed on the basis of the design data (CAD data, etc.) of the semiconductor manufacture device, appropriate parameter setting can be executed on the basis of visual comparison with precise design data.

As mentioned above, according to the present invention, the process or input operation relating to the template matching art used for inspection positioning so far can be reduced remarkably and a scanning electron microscope can be operated with high precision at high speed.

What is claimed is:

1. A scanning electron microscope for detecting a pattern on the basis of electrons obtained by scanning an electron beam on a sample and identifying a desired position on the basis of said detected pattern and a pattern registered beforehand, wherein:

said microscope has means for setting information concerning a pattern kind, an interval between a plurality of parts constituting said pattern, and a size of parts constituting said pattern and means for forming a pattern image composed of a plurality of parts on the basis of said information obtained by said means.

2. A scanning electron microscope according to claim 1, wherein said pattern is formed by a plurality of line patterns or a plurality of hole patterns.

3. A scanning electron microscope according to claim 1, wherein said microscope has means for executing template matching on the basis of said formed pattern and said pattern detected on the basis of electrons obtained by scanning an electron beam on a sample.

4. A scanning electron microscope for detecting a pattern on the basis of electrons obtained by scanning an electron beam on a sample and identifying a desired position on the basis of said detected pattern and a pattern registered beforehand, wherein:

said microscope has means for recognizing a number of said detected patterns and means for calculating an evaluation value on the basis of comparison of said number recognized by said means with a number of said registered patterns.

5. A scanning electron microscope for detecting a pattern on the basis of electrons obtained by scanning an electron beam on a sample and identifying a desired position on the basis of said detected pattern and a pattern registered beforehand, wherein:

said microscope has means for recognizing an interval between a plurality of parts of said detected pattern and means for calculating, on the basis of comparison of said interval recognized by said means with an interval between said parts of said registered patterns, an evaluation value based on consistency.

6. A scanning electron microscope according to claim 4, wherein said microscope has means for skipping measurement at said desired position when said obtained evaluation value is smaller than a certain value.

7. A scanning electron microscope according to claim 4, wherein said microscope has display means for displaying said evaluation value.

8. A scanning electron microscope according to claim 5, wherein said microscope has means for skipping measurement at said desired position when said obtained evaluation value is smaller than a certain value.

9. A scanning electron microscope according to claim 5, wherein said microscope has display means for displaying said evaluation value.

* * * * *